US012070204B2

(12) United States Patent
Christakis et al.

(10) Patent No.: US 12,070,204 B2
(45) Date of Patent: Aug. 27, 2024

(54) APPARATUS, DEVICE, AND METHOD FOR INCREASING FORCE DISTRIBUTION AT SUTURE-TISSUE INTERFACE

(71) Applicant: Boston Scientific Scimed, Inc., Maple Grove, MN (US)

(72) Inventors: Laura E. Christakis, Framingham, MA (US); Paul Smith, Smithfield, RI (US); Ryan V. Wales, Northborough, MA (US); Scott E. Brechbiel, Acton, MA (US); Jeff Gray, Sudbury, MA (US); Sean P. Fleury, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 654 days.

(21) Appl. No.: 16/897,561

(22) Filed: Jun. 10, 2020

(65) Prior Publication Data

US 2020/0390436 A1 Dec. 17, 2020

Related U.S. Application Data

(60) Provisional application No. 62/860,108, filed on Jun. 11, 2019.

(51) Int. Cl.
*A61B 17/04* (2006.01)

(52) U.S. Cl.
CPC ...... *A61B 17/0469* (2013.01); *A61B 17/0401* (2013.01); *A61B 2017/0406* (2013.01); *A61B 2017/0409* (2013.01); *A61B 2017/047* (2013.01); *A61B 2017/0479* (2013.01)

(58) Field of Classification Search
CPC ........ A61B 17/0469; A61B 2017/0409; A61B 17/0482; A61B 2017/0495; A61B 17/0491; A61B 2017/0496; A61B 2017/0464

USPC .......................................................... 606/145
See application file for complete search history.

(56) References Cited

U.S. PATENT DOCUMENTS

| 6,500,194 | B2 | 12/2002 | Benderev et al. |
| 7,063,715 | B2 * | 6/2006 | Onuki ............... A61B 17/0401 |
| | | | 606/220 |
| 8,574,243 | B2 | 11/2013 | Saadat et al. |
| 8,579,935 | B2 | 11/2013 | DeVries et al. |
| 8,961,545 | B2 | 2/2015 | Kelleher et al. |
| 9,237,889 | B2 | 1/2016 | Dumanian et al. |

(Continued)

FOREIGN PATENT DOCUMENTS

| WO | 2005086945 A2 | 9/2005 |
| WO | 2019108261 A1 | 6/2019 |

OTHER PUBLICATIONS

International Search Report and Written Opinion for the International Patent Application No. PCT/US2020/036957, mailed Sep. 29, 2020, 22 pages.

*Primary Examiner* — Kathleen S Holwerda
*Assistant Examiner* — Serenity A Miller
(74) *Attorney, Agent, or Firm* — Seager, Tufte & Wickhem, LLP

(57) ABSTRACT

The present disclosure relates generally to apparatus, devices, and methods for increasing force distribution at a suture-tissue interface. In some embodiments, a tissue suturing device may include a deployment device and a plurality of tissue supports deployable from the deployment device towards a target tissue. The plurality of tissue supports may each include a central opening for receiving a suture during deployment.

8 Claims, 21 Drawing Sheets

(56) References Cited

U.S. PATENT DOCUMENTS

| | | |
|---|---|---|
| 9,675,352 B2 | 6/2017 | DeVries et al. |
| 10,045,871 B2 | 8/2018 | Saadat et al. |
| 2002/0193816 A1 | 12/2002 | Laufer et al. |
| 2004/0249367 A1* | 12/2004 | Saadat ................. A61B 1/2736 600/101 |
| 2005/0251153 A1 | 11/2005 | Sakamoto et al. |
| 2006/0085036 A1* | 4/2006 | Viola ............... A61B 17/00491 606/228 |
| 2007/0049929 A1 | 3/2007 | Catanese et al. |
| 2011/0118758 A1 | 5/2011 | Sauer |

\* cited by examiner

1600

| PASSING A NEEDLE AND A SUTURE OF A TISSUE SUTURING DEVICE THROUGH A TARGET TISSUE, THE TISSUE SUTURING DEVICE EXTENDING FROM A DISTAL END OF AN ENDOSCOPE | 1601 |

| DEPLOYING A FIRST TISSUE SUPPORT FROM THE TISSUE SUTURING DEVICE TO A POSITION ALONG A FIRST PORTION OF THE TARGET TISSUE | 1603 |

| DEPLOYING A SECOND TISSUE SUPPORT FROM THE TISSUE SUTURING DEVICE TO A POSITION ALONG A SECOND PORTION OF THE TARGET TISSUE, WHEREIN TIGHTENING THE SUTURE BRINGS THE FIRST TISSUE SUPPORT AND SECOND TISSUE SUPPORT CLOSER TOGETHER | 1605 |

FIG. 16

APPARATUS, DEVICE, AND METHOD FOR INCREASING FORCE DISTRIBUTION AT SUTURE-TISSUE INTERFACE

CROSS-REFERENCE TO RELATED APPLICATIONS

The present application claims the benefit of priority under 35 U.S.C. § 119 to U.S. Provisional Patent Application 62/860,108, filed Jun. 11, 2019, which application is incorporated herein by reference in its entirety for all purposes.

FIELD

The present disclosure relates generally to suturing devices and, more particularly, to suturing devices for increasing force distribution at a suture-tissue interface.

BACKGROUND

Suturing is used during a wide variety of endoscopic procedures, such as closing a wound, anchoring a stent or other implant, or shorting curvature in the stomach. Several types of sutures and devices for implantation and extraction have been developed. In some approaches, suturing is performed by repeatedly passing a sharp suture needle attached to a length of suture material through portions of tissue to be sutured together. The free ends of the suture material are then tied together to complete the suturing procedure.

Many endoscopic procedures pull tissue together and hold the tissue in a new configuration. However, reconfiguring and constraining tissue generates tension between the tissue and the suture. While current sutures and suturing approaches may provide an adequate temporary solution to holding tissue, over time the force required to hold the tissue in place becomes too great to sustain an equilibrium. As a result, when the tissue relaxes the suture can tear through the tissue. It is with the above considerations in mind that the improvements of the present disclosure may be useful.

SUMMARY

The present disclosure in its various embodiments relates generally to apparatuses, devices, and methods for redistributing force at the tissue-suture interface to increase long-term effectiveness of an endoscopic suturing procedure.

In one or more embodiments, a tissue suturing apparatus for use with an endoscope may include a tissue suturing device coupleable to a distal end of the endoscope, the tissue suturing device comprising a plurality of tissue supports, wherein each of the plurality of tissue supports is deployable towards a target tissue, and wherein one or more tissue supports of the plurality of tissue supports receives a suture during deployment. In some embodiments, the tissue suturing device may further include a needle, wherein the needle engages a tissue support of the plurality of tissue supports to deploy the tissue support. In some embodiments, the tissue suturing apparatus may further include a collar extending from a fixed end of the tissue suturing device, wherein the collar defines a collar opening aligned with a working channel of the endoscope, and wherein each of the plurality of tissue supports extends around an exterior of the collar prior to deployment. In some embodiments, the deployment device may include a housing containing the plurality of tissue supports, and a cover extending across the housing, the cover including an opening to permit access to the plurality of tissue supports by a needle attached to the suture. In some embodiments, the deployment device may include an interior channel and a biasing device for biasing the plurality of tissue supports within the interior channel, wherein the plurality of tissue supports are arranged end-to-end within the interior channel. In some embodiments, the deployment device may include a mandrel defining a central channel, wherein each of the plurality of tissue supports is disposed concentrically around the mandrel. In some embodiments, the suture may include a core and a sheath, wherein the sheath is operable to expand radially from the core in an area adjacent the target tissue. In some embodiments the sheath may include a plurality of flexible strands. In some embodiments, the plurality of tissue supports may include one or more of the following: a flexible washer, a sprayable adhesive, a pledget, and a spring-loaded wire.

In one or more embodiments, a tissue suturing device may include a deployment device and a plurality of tissue supports deployable from the deployment device towards a target tissue. The plurality of tissue supports may include a central opening for receiving a suture during deployment. In some embodiments, the tissue suturing device may further include a fixed end secured to a distal end of an endoscope, and a free end opposite the fixed end, wherein the deployment device is coupled to one of: the fixed end, and the free end. In some embodiments, the deployment device may include a collar extending from the fixed end, wherein the collar defines a collar opening aligned with a working channel of the endoscope, and wherein each of the plurality of tissue supports extends around an exterior of the collar prior to deployment. In some embodiments, the deployment device may include a housing surrounding the plurality of tissue supports, and a cover extending across the housing, the cover including an opening to permit access to the plurality of tissue supports by a needle attached to the suture. In some embodiments, the housing may include an interior channel and a biasing device for biasing the plurality of tissue supports within the interior channel, wherein the plurality of tissue supports are arranged end-to-end within the interior channel.

In one or more embodiments, a method may include passing a needle and a suture of a tissue suturing device through a target tissue, the tissue suturing device extending from a distal end of an endoscope. The method may further include deploying a first tissue support from the tissue suturing device to a position along a first portion of the target tissue, and deploying a second tissue support from the tissue suturing device to a position along a second portion of the target tissue, wherein tightening the suture brings the first tissue support and second tissue support closer together. In some embodiments, the method may further include housing a plurality of tissue supports within a deployment device, wherein the first tissue support is exposed within a suture cavity, engaging the first tissue support within the suture cavity by the needle to remove the first tissue support from the deployment device, exposing the second tissue support within the suture cavity, and engaging the second tissue support within the suture cavity by the needle to remove the second tissue support from the deployment device. In some embodiments, the method may further include accessing the plurality of tissue supports through an opening of a cover extending across the deployment device. In some embodiments, the method may further include biasing the plurality of tissue supports towards the suture cavity using a biasing device. In some embodiments, the method may include removing the first tissue support from the tissue suturing device using a set of prongs, removing the first tissue support from the set of prongs and onto the suture, removing the second tissue support from the tissue suturing device using the set of prongs, and removing the second tissue support from the set of prongs and onto the suture.

Various one or more of the features summarized above may be interchanged, exchanged, combined or substituted with or for other features summarized above, for use in connection with the apparatuses, devices, and methods summarized above, and with respect to the embodiments described in greater detail below and embodiments otherwise within the scope of the present disclosure.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. Furthermore, some of the figures include cross-sectional views in the form of "slices", or "near-sighted" cross-sectional views, omitting certain background lines or features otherwise visible in a "true" cross-sectional view, for illustrative clarity. In the figures:

FIG. 16 is a flow diagram of a method according to embodiments of the present disclosure.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Embodiments herein disclose endoscopic tissue suturing apparatuses, devices, and methods for increasing force distribution at a suture-tissue interface. Those skilled in the art will appreciate that while the approaches of the present disclosure will herein be described with reference to suturing an area of the stomach, the approaches may be utilized in other gastrointestinal transluminal procedures, and may be introduced transorally as well as transanally.

Although non-limiting, approaches of the present disclosure may be effective for treating gastroesophageal reflux disease (GERD) by performing procedures such as partial circumferential endoscopic mucosal resection (EMR) or submucosal dissection (ESD) of a patient's gastrointestinal tract.

Figure 1:
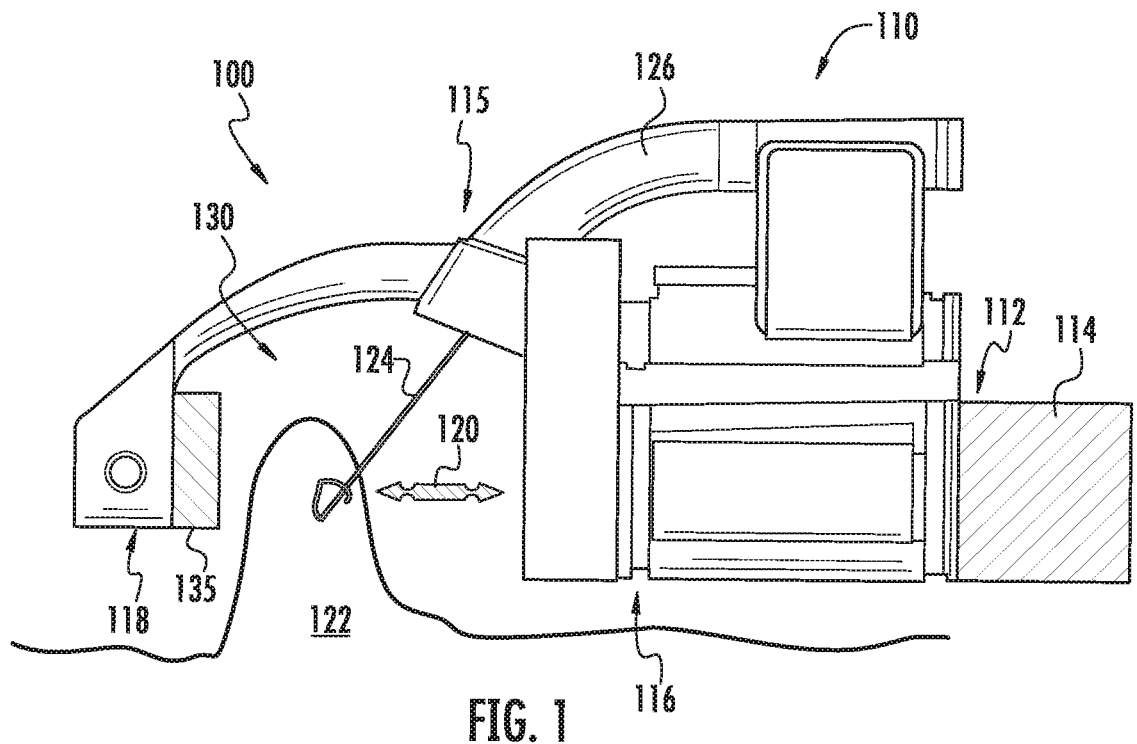
FIG. 1 is a side view of a tissue suturing apparatus according to embodiments of the present disclosure.

Turning now to FIG. 1, a tissue suturing apparatus (hereinafter "apparatus") 100 according to embodiments of the present disclosure will be described. As shown, the apparatus 100 may include a tissue suturing device (hereinafter "device") 110 extending from a distal end 112 of a scope, such as an endoscope 114. The device 110 may be used with other types of scopes as well, such as bronchoscopes, duodenoscopes, gastroscopes, colonoscopes, etc. The device 110 may include a head or cap 115 having a fixed end 116 directly coupled to the endoscope 114, and a free end 118 opposite the fixed end 116. In some embodiments, the cap 115 may be coupled to the endoscope 114 using a variety of techniques, such as by mechanical fasteners, glue, suture, press fit, tape, overmolding, etc. In other embodiments, the dispenser cap may be integrally formed with the endoscope.

During use, a needle 120 may be passed back and forth between the fixed end 116 and the free end 118 along a longitudinal axis, the needle 120 including one or more pointed tips for puncturing a target tissue 122 with each pass. In some embodiments, a tissue grasper 124 may be delivered through a channel 126 of the cap 115 to engage the target tissue 122, bringing the target tissue 122 into a suture cavity 130 located between the fixed end 116 and the free end 118.

The device 110 may include a deployment device 135 containing a plurality of tissue supports (not shown) therein. As will be explained in greater detail below, the tissue supports may be added between a suture and the target tissue 122 during one or more passes of the needle 120. In some embodiments, the deployment device 135 may be coupled to the free end 118 of the device 110, positioned generally opposite the fixed end 116.

Figure 2:
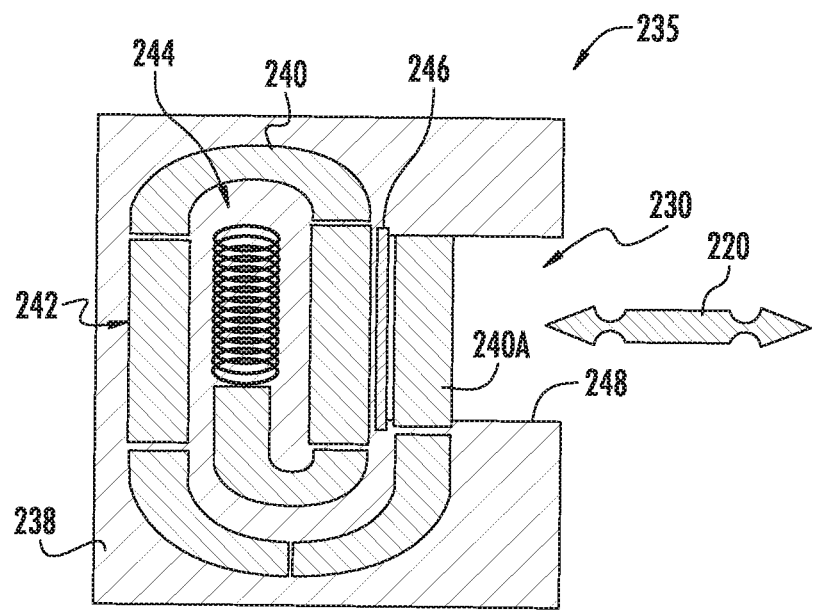
FIG. 2 is a side cross-sectional view of an example deployment device of the tissue suturing apparatus of FIG. 1, according to embodiments of the present disclosure.

Turning now to FIG. 2, an example deployment device 235 according to embodiments of the present disclosure will be described. As shown, the deployment device 235 may be a cartridge including a housing 238 containing a plurality of tissue supports 240 therein. The housing 238 may include an interior channel 242 and a biasing device 244 (e.g., a spring) for biasing the plurality of tissue supports 240 through the interior channel 242. In some embodiments, the plurality of tissue supports 240 are solid, flexible components arranged end-to-end. During suturing, a needle 220 enters a suture cavity 230, puncturing an exposed tissue support 240A of the plurality of tissue supports 240. As the exposed tissue support 240A is brought away from the deployment device 235, attached to the needle 220, the biasing device 244 may cause the next tissue support of the plurality of tissue supports 240 to enter the suture cavity 230 for subsequent engagement by the needle 220 on the next pass. One or more of the plurality of tissue supports 240 may be added every time the needle 220 passes through the tissue such that the interface between a suture and the tissue becomes more robust as the procedure continues. In some embodiments, the deployment device 235 may include a rigid plate 246 positioned behind the exposed tissue support 240A to prevent the needle 220 from extending into the housing 238. Furthermore, the deployment device 235 may include an overhang 248, which may keep the exposed tissue support 240A aligned within the suture cavity 230.

Figure 3A:
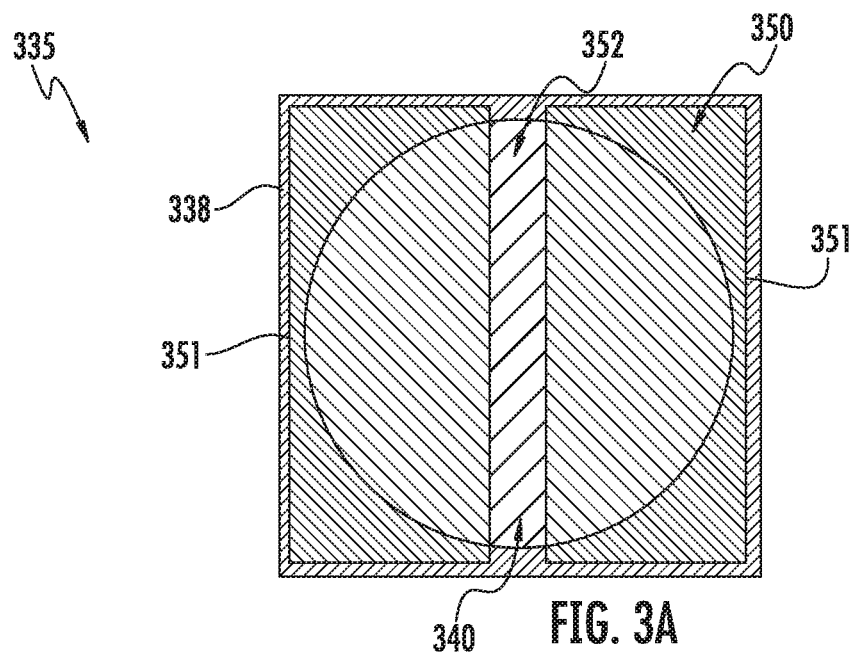
FIG. 3A is a front view of an example covering over the deployment device of FIG. 2, according to embodiments of the present disclosure.
Figure 3B:
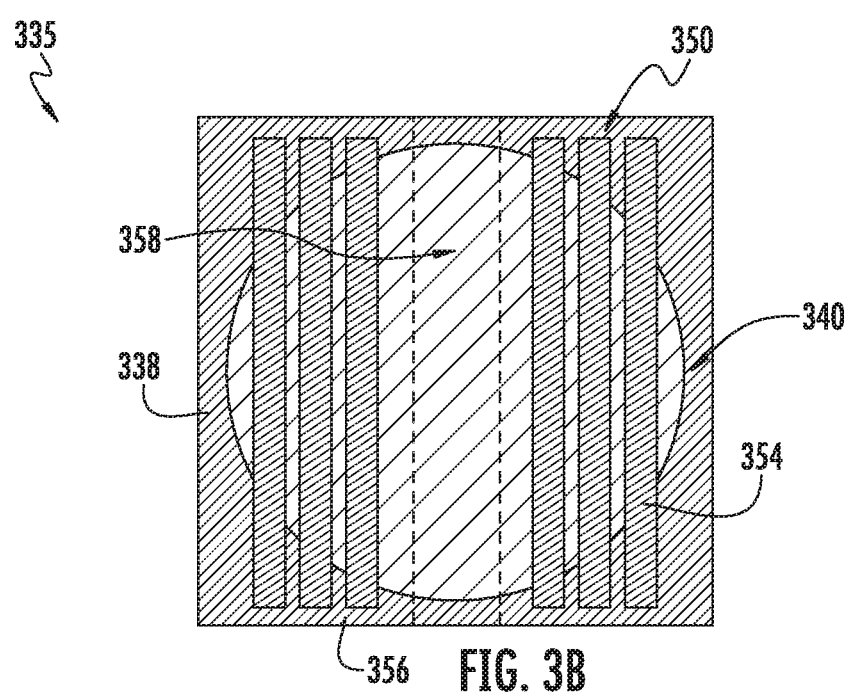
FIG. 3B is a front view of an example covering over the deployment device of FIG. 2, according to embodiments of the present disclosure.

Turning now to FIGS. 3A-3B, various deployment devices according to embodiments of the present disclosure will be described in greater detail. As shown, a deployment device 335 may include a plurality of tissue supports 340 stacked atop one another within a housing 338. The deployment device 335 may include a cover 350 extending across the housing 338. In the embodiment of FIG. 3A, the cover 350 may include one or more membranes 351 extending across the housing 338. The membrane(s) 351 may define a slot or opening 352 to permit access to the plurality of tissue supports 340 by a needle (not shown). The membrane(s) 351 may be durable enough to hold the plurality of tissue supports 340 in place within the deployment device 335, yet flexible enough to allow an exposed tissue support of the plurality of tissue supports 340 to be pulled from the deployment device 335 by the needle.

In the embodiment of FIG. 3B, the cover 350 may include a plurality of components, such as slats 354 extending across a frame 356 of the housing 338 to hold the plurality of tissue supports 340 in place. In various examples, the plurality of slats 354 may be oriented laterally, longitudinally and/or diagonally. As shown, the plurality of slats 354 may define an opening 358 to allow a needle to enter the deployment device 335 and puncture an exposed tissue support of the plurality of tissue supports 340. The exposed tissue support may then be folded or bent, and then pulled through the opening 358.

Figure 4A:
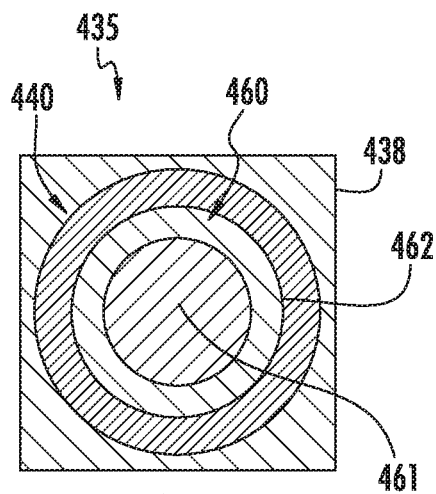
FIG. 4A is an end view of an example deployment device of the tissue suturing apparatus of FIG. 1, according to embodiments of the present disclosure.

As shown in FIG. 4A, a deployment device 435 may include a mandrel 460 within a housing 438. In some embodiments, the mandrel 460 may be a tubular shaped component defining a central channel 461 therein. As will be described in greater detail below, the central channel 461 permits a needle to enter the deployment device 435 and retain one or more of a plurality of tissue supports 440. In this embodiment, the plurality of tissue supports 440 may be cylindrical washers disposed concentrically around an exterior surface 462 of the mandrel 460. Furthermore, the plurality of tissue supports 440 may elastically expand to fit the mandrel 460 in the deployment device 435. After deployment, the plurality of tissue supports 440 may shrink or constrict to effectively close around a suture.

Figure 4B:
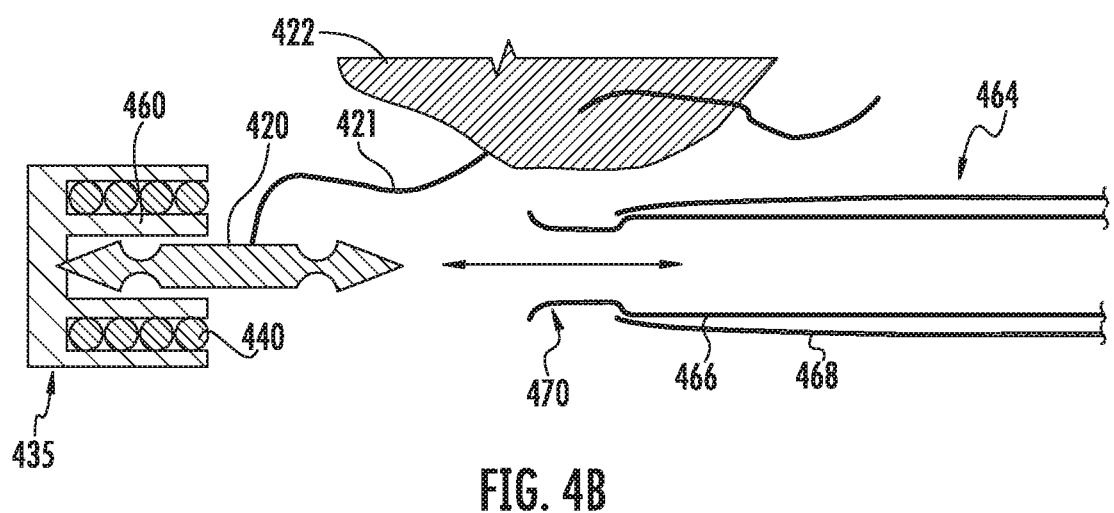
FIGS. 4B-4E are side cross-sectional views demonstrating a process for using the deployment device of FIG. 4A, according to embodiments of the present disclosure.

Turning now to FIGS. 4B-4E, cross-sectional views demonstrating operation of the deployment device 435 of FIG. 4A will be described in greater detail. As shown in FIG. 4B, the deployment device 435 contains a plurality of tissue supports 440 (e.g., four) disposed around the mandrel 460. The deployment device 435 may operate with a needle shuttling system 464, which may include two or more nested hypo-tubes, such as an inner tube 466 and an outer tube 468 operable to shuttle a needle 420 and a suture 421 back and forth through a target tissue 422. In some embodiments, a set of prongs 470 may extend from the inner tube 466. In various examples, the inner tube 466 and the outer tube 468 may move together or independently.

Figure 4C:
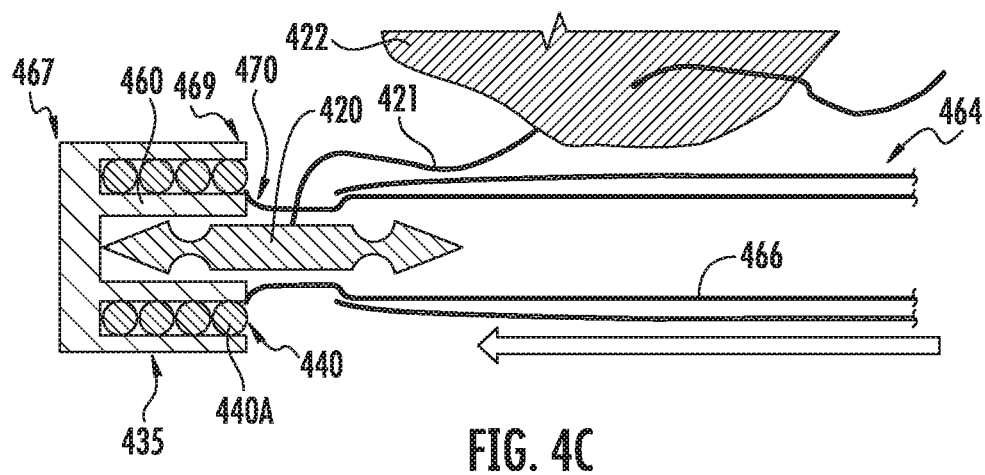

As shown in FIG. 4C, the inner tube 466 of the needle shuttling system 464 may be passed distally over the needle 420 to interact with the deployment device 435. For example, the prongs 470 on the end of the inner tube 466 may be deformable to fit alongside/adjacent the plurality of tissue supports 440. In some embodiments, a depth that the prongs 470 enter the deployment device 435 can be controlled at the handle (not shown) by an operator. In other embodiments, the prongs 470 merely abut a proximal end 469 of the deployment device 435. Although not shown, the deployment device 435 may include a spring system (e.g., one or more springs, or other biasing mechanisms) incorporated into a distal end 467 of the deployment device 435 to continually or selectively push the plurality of tissue supports 440 to the proximal end 469 for engagement with the prongs 470. For example, in response to the needle being received in the deployment device 435, a proximal-most tissue support 440 may be deployed onto the prongs 470.

Figure 4D:
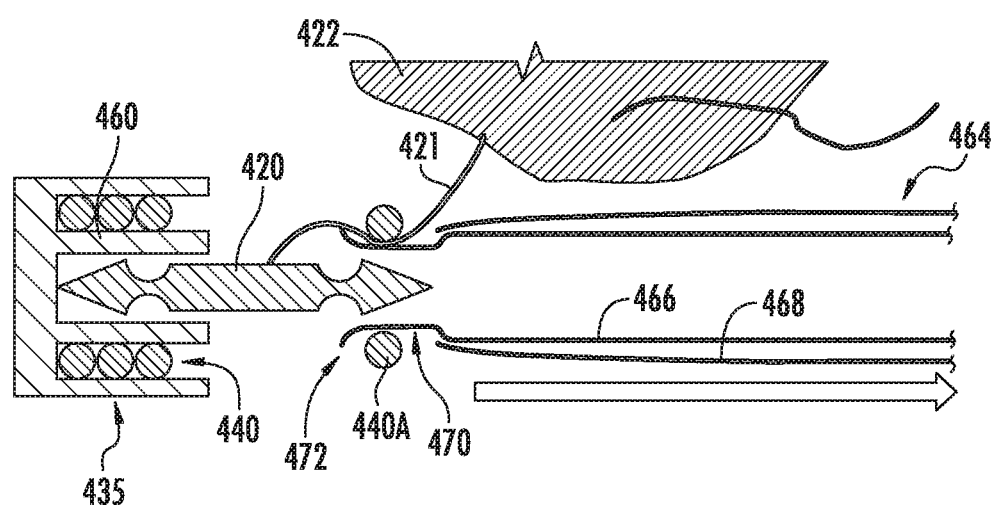

When the needle shuttling system 464 is retracted from the deployment device 435, an outermost tissue support 440A of the plurality of tissue supports 440 may be removed from the mandrel 460, for example, as shown in FIG. 4D. In some embodiments, the outermost tissue support 440A may extend around the suture 421 and remain on the prongs 470 while the inner tube 466 moves farther away from the deployment device 435. The outermost tissue support 440A may contract, thereby remaining on the prongs 470 by tension. Furthermore, the prongs may include one or more curved ends 472 (e.g., curved radially outward) to prevent the outermost tissue support 440A from sliding off the prong 470.

Figure 4E:
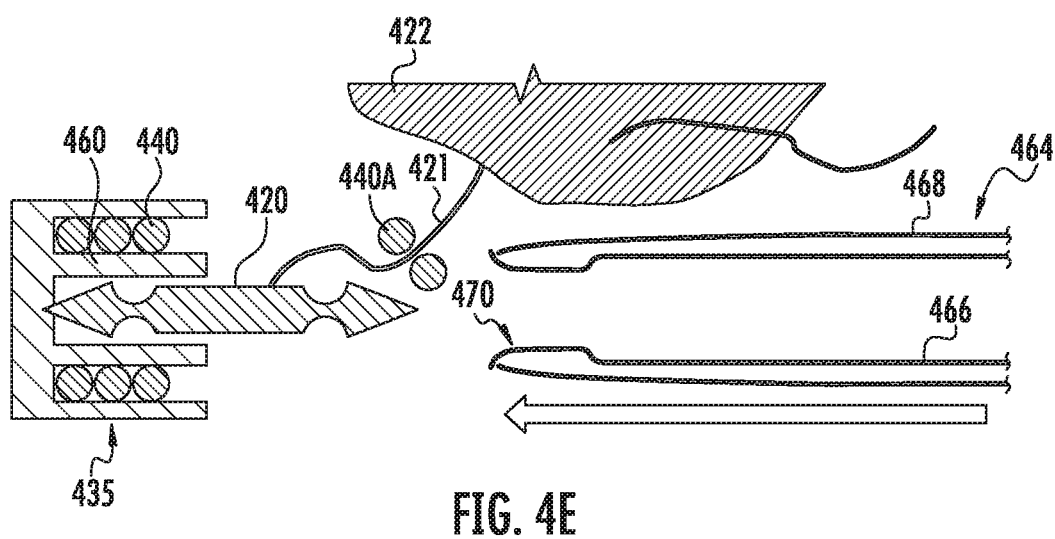

Next, as shown in FIG. 4E, the outer tube 468 of the needle shuttling system 464 may be advanced distally in relation to the inner tube 466, pushing the outermost tissue support 440A off the prongs 470 and onto the suture 421, for example, between the needle 420 and the target tissue 422. The position of the outer tube 468 can then be reset in relation to the inner tube 466 so the needle shuttling system 464 is ready for another needle pass. In some embodiments, a tissue support may not be added in between each suture pass. Furthermore, it will be appreciated that the number of tissue supports deployed depends on the needs of the procedure, physician, and/or the capacity of the deployment device 435. Embodiments herein are not limited in this context.

Figure 5:
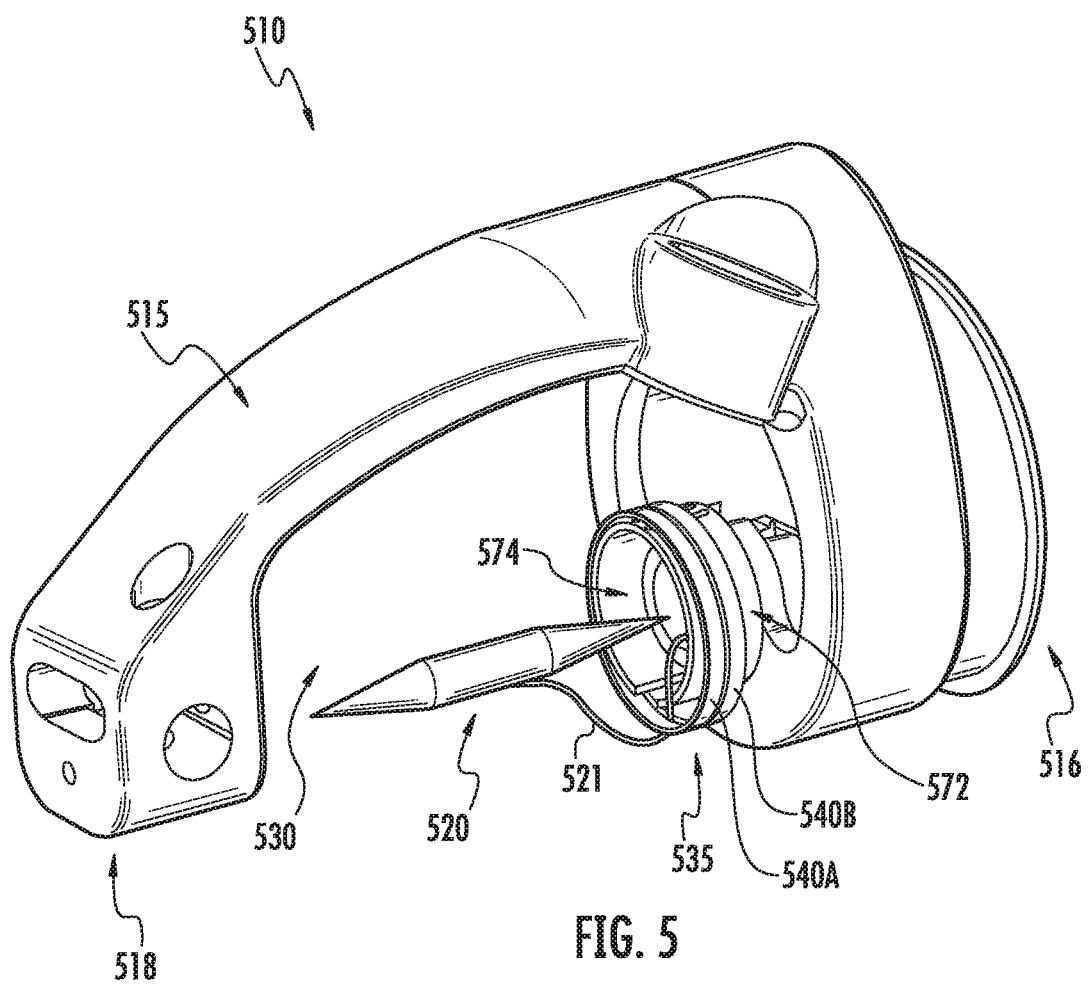
FIG. 5 is a perspective view of an example deployment device according to embodiments of the present disclosure.
Figure 6:
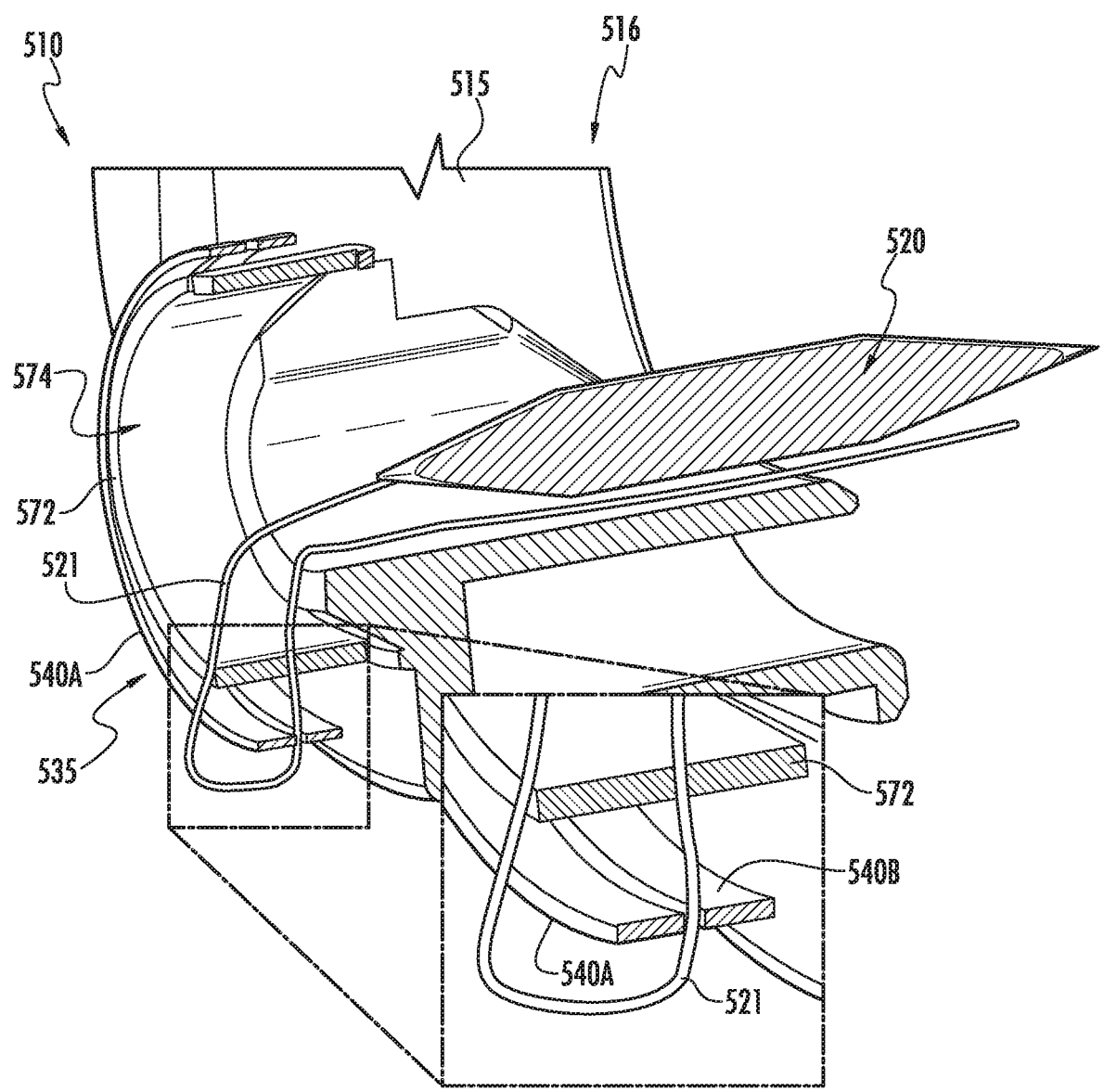
FIG. 6 is a partial cross-sectional perspective view of the deployment device of FIG. 5, according to embodiments of the present disclosure.

Turning now to FIGS. 5-6, a tissue suturing device (hereinafter "device") 510 according to embodiments of the present disclosure will be described. The device 510 may include a head or cap 515 having a fixed end 516 coupleable with an endoscope (not shown), and a free end 518 opposite the fixed end 516. In some embodiments, the cap 515 may be integrally formed with an endoscope or other instrument. During use, a needle 520 and a suture 521 may be passed back and forth between the fixed end 516 and the free end 518 along a longitudinal axis, puncturing a target tissue (not shown) positioned in a suture cavity 530.

As further shown, the device 510 may include a deployment device 535 coupled to the fixed end 516 of the cap 515. In this embodiment, the deployment device 535 may include a plurality of tissue supports 540A-540B extending around a collar 572. During assembly, the suture 521, which is connected to the needle 520, may be threaded between tissue support 540A and tissue support 540B to allow distal most positioned tissue support 540A to be placed between the needle 520 and the tissue.

As shown, the collar 572 may secure the device 510 onto a distal end of the endoscope. In other embodiments, the collar 572 is integrally formed with the endoscope or other tubular instrument. Although non-limiting, each of the plurality of tissue supports 540A-540B may be a washer-shaped support disposed around an exterior of the collar 572. The collar 572 may define a collar opening 574 aligned with a working channel of the endoscope. The needle 520 may pass in and out of the collar opening 574 during suturing, as will be described in greater detail below. While situated on the collar 572, the plurality of tissue supports 540 are stretched for deployment over the needle 520 and the suture 521. As the suture 521 is pulled at the proximal handle of the device 510, each of the plurality of tissue supports 540 may be deployed separately. Advantageously, the plurality of tissue supports 540A-540B may be deployed on opposite sides of the target tissue being tensioned together, for example, after the operator has passed the needle 520 through the target tissue a desired number of times but before the suture 521 is cinched.

In some embodiments, the plurality of tissue supports 540 are deployed using an additional suture (not shown). For example, the additional suture may be connected to one or more of the plurality of tissue supports 540A-540B. As the additional suture is pulled towards the fixed end 516, the additional suture may release distal most positioned tissue support 540A from the collar 572. In some embodiments, the collar 572 may include an aperture (not shown) through a sidewall thereof, the aperture allowing the additional suture to exit from the central bore of the collar 572. Having the plurality of tissue supports 540A-540B situated on the collar 572 with the additional suture may allow the needle 520 to shuttle back and forth normally as many times as the operator needs.

Figure 7A:
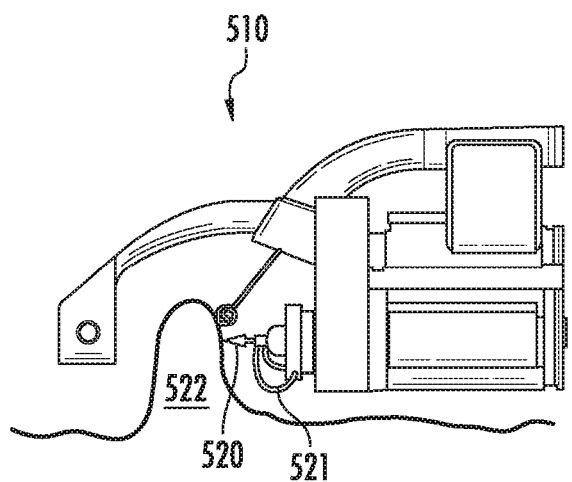
FIGS. 7A-7I are side views demonstrating a process for using the deployment device of FIGS. 5-6, according to embodiments of the present disclosure.
Figure 7B:
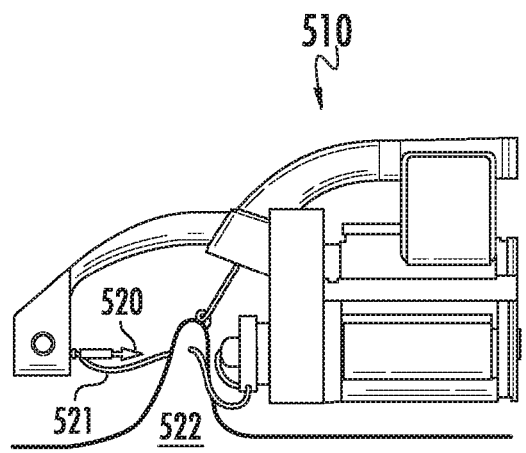
Figure 7C:
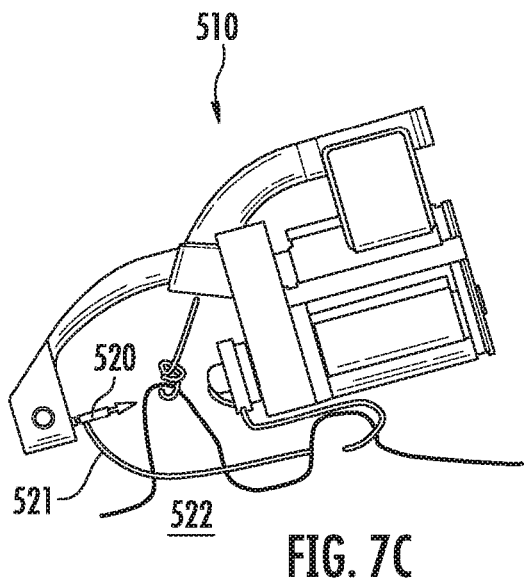
Figure 7D:
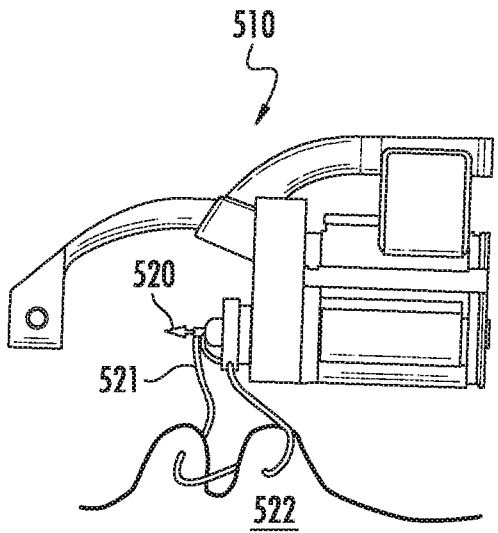
Figure 7E:
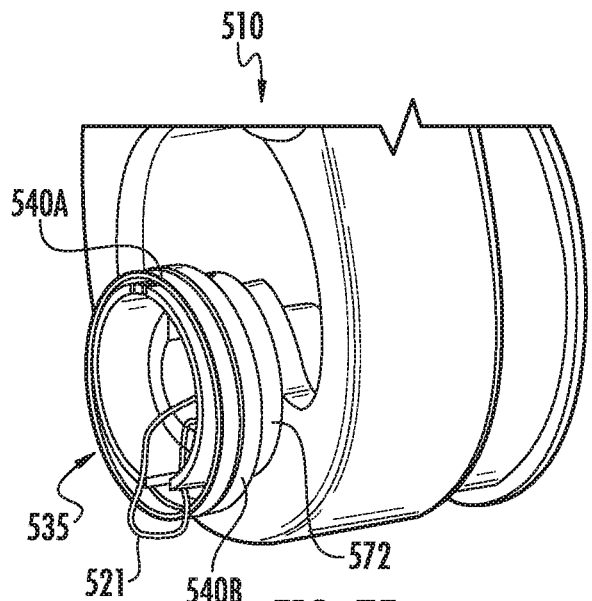
Figure 7F:
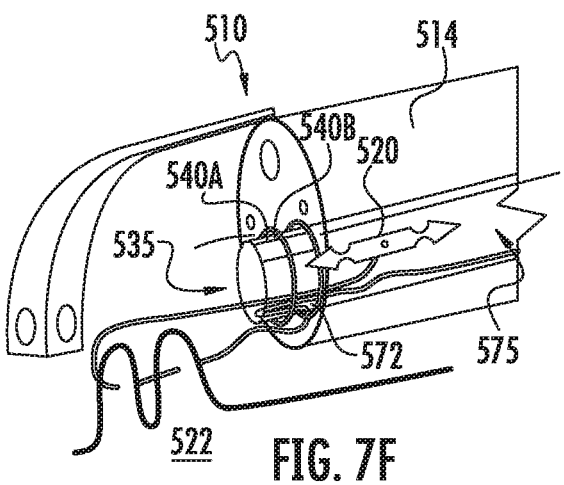
Figure 7G:
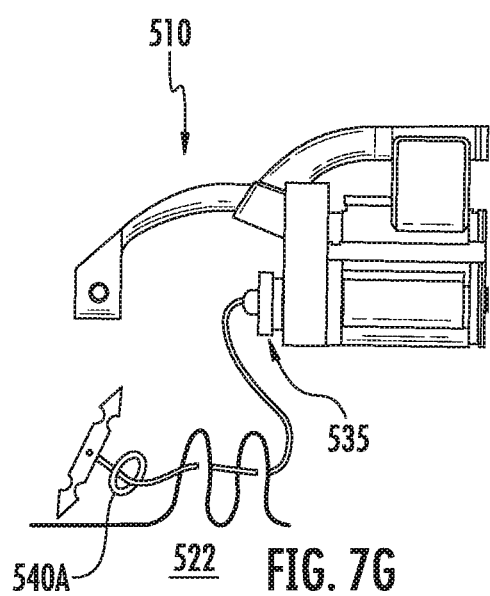
Figure 7H:
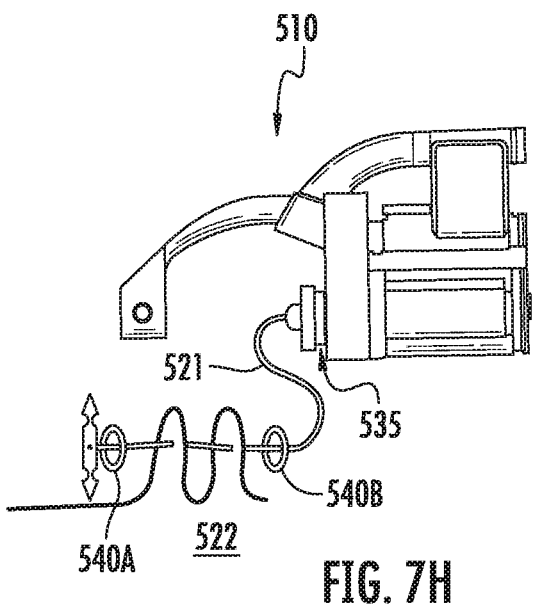
Figure 7I:
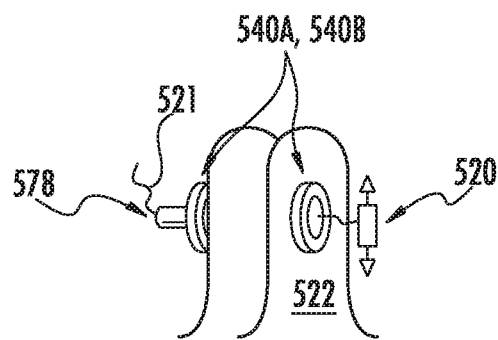

Turning now to FIGS. 7A-7H, operation of the device 510 according to embodiments of the present disclosure will be described in greater detail. In FIGS. 7A-7B, the needle 520 and the suture 521 may be passed through a first piece of the target tissue 522, and then through a second piece of the target tissue 522, as demonstrated in FIGS. 7C-7D. As shown in FIGS. 7E-7F, the needle 520 may then be pulled through the collar 572 of the deployment device 535 and into a working channel 575 of an endoscope 514. In some embodiments, the suture 521 may extend around just the distal most positioned tissue support 540A. During deployment, as demonstrated in FIG. 7G, the distal most positioned tissue support 540A may be released from the deployment device 535 and then brought into position on one side of the target tissue 522. A second tissue support 540B may then be released from the deployment device 535, and then brought into position on an opposite side of the target tissue 522, as shown in FIG. 7H. In some embodiments, the endoscope 514 (FIG. 7F) may be move away from the target tissue 522 to bring the needle 520 into contact with one side of the target tissue 522, while the suture 521 pulled to deploy the second tissue support 540B onto the suture 521. Finally, as shown in FIG. 7I, the suture 521 may be pulled tight and secured, for example, using a cinching device 578. The cinching device 578 may bring the distal most positioned tissue support 540A and second tissue support 540B on opposite sides of the target tissue 522 closer together by pulling the suture 521 to bring the needle 520 towards the deployment device 535.

Figure 8A:
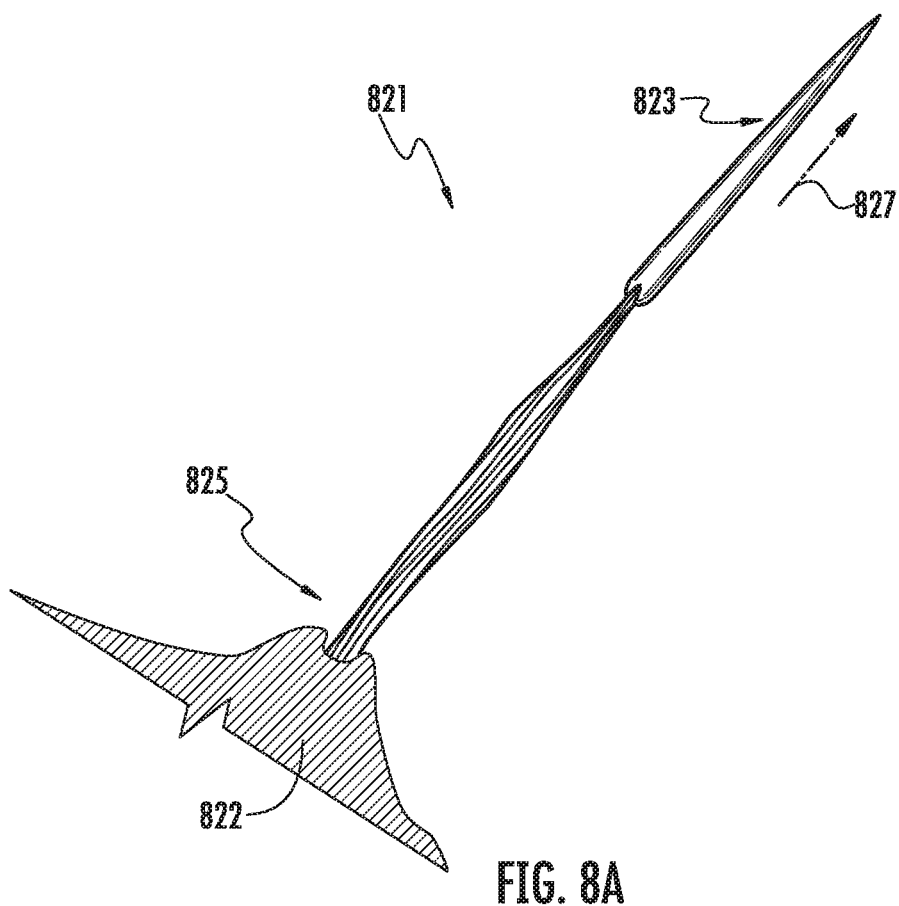
FIGS. 8A-8D are perspective views demonstrating use of an example suture according to embodiments of the present disclosure.
Figure 8B:
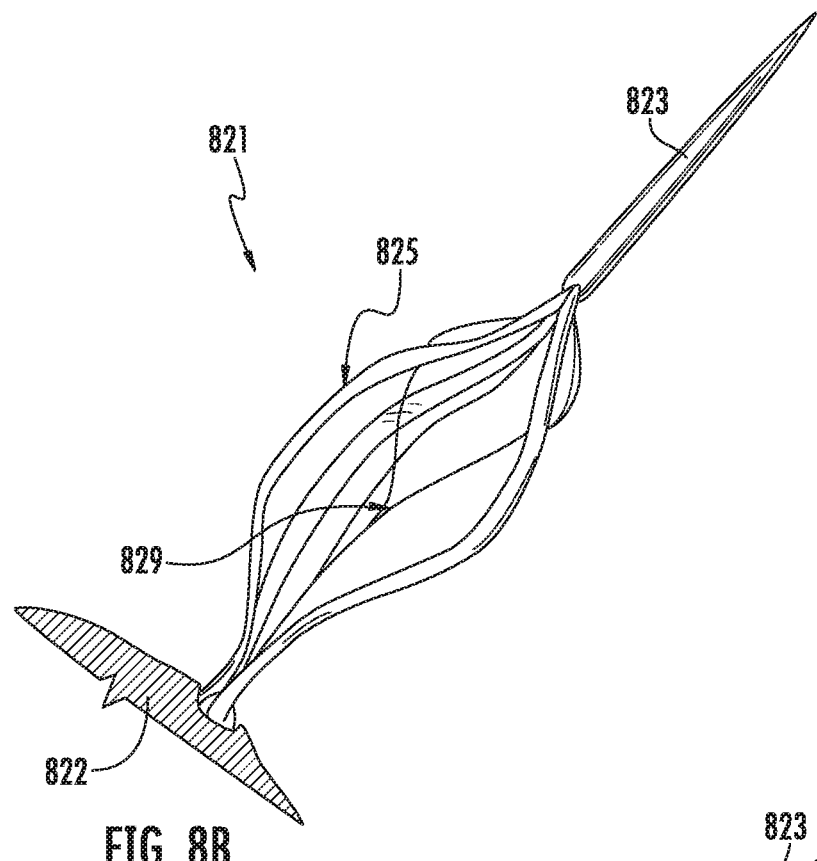
Figure 8C:
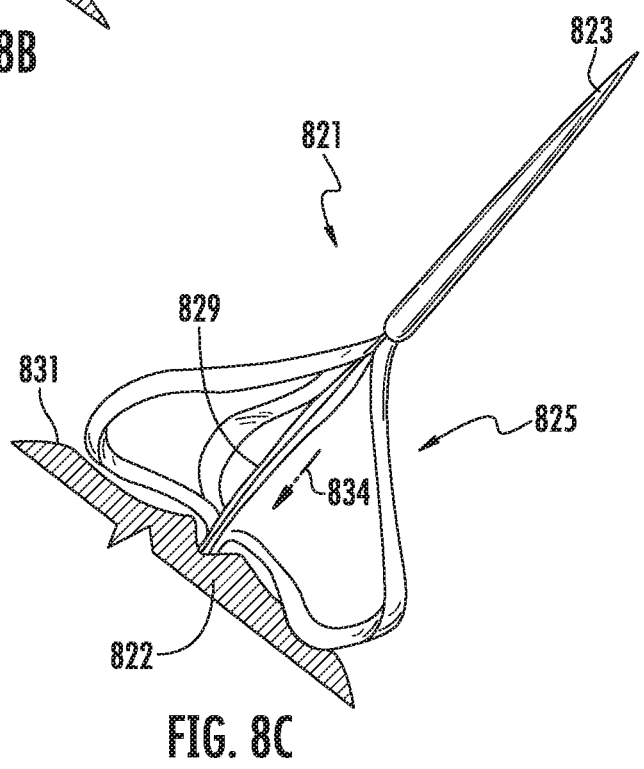
Figure 8D:
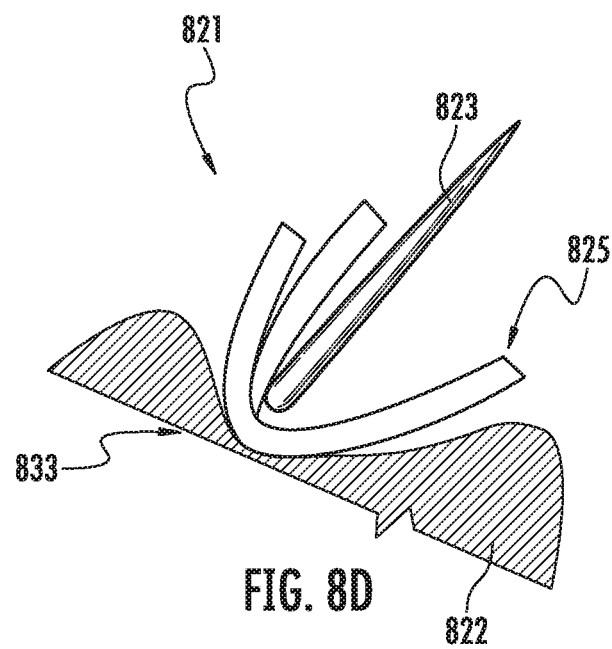

Turning now to FIGS. 8A-8D, a suture 821 according to embodiments of the present disclosure will be described. The suture 821 may include a rigid or semi-rigid tip 823 operable to pierce a target tissue 822. The rigid tip 823 may be connected to a plurality of flexible strands or filaments 825. As shown in FIG. 8A, the suture 821 may initially pass through the target tissue 822 in a direction demonstrated by arrow 827. In this configuration, the filaments are generally straight and elongated. As demonstrated in FIG. 8B, the suture 821 may include one or more retention wires 829 surrounding the filaments 825. The retention wires 829 may be used to pull the suture 821 back towards the target tissue 822, for example, in a direction shown by arrow 834 in FIG. 8C. Pulling the suture 821 toward the target tissue 822 causes the filaments 825 to extend radially, creating a malecot configuration against a surface 831 of the target tissue 822. As shown in FIG. 8D, an interface 833 between the filaments 825 and the target tissue 822 may generally have larger area due the expanded configuration of filaments 825. Force is therefore better distributed at the interface 833, making it less likely that the target tissue 822 will rupture.

Figure 9A:
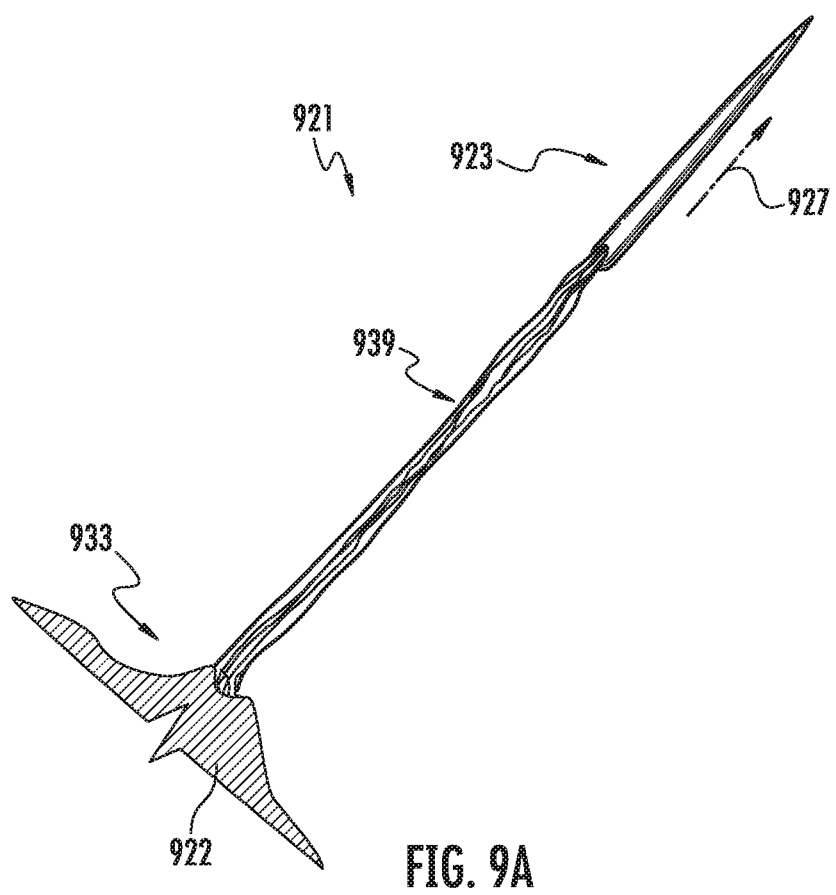
FIGS. 9A-9D are perspective views demonstrating use of an example suture according to embodiments of the present disclosure.
Figure 9B:
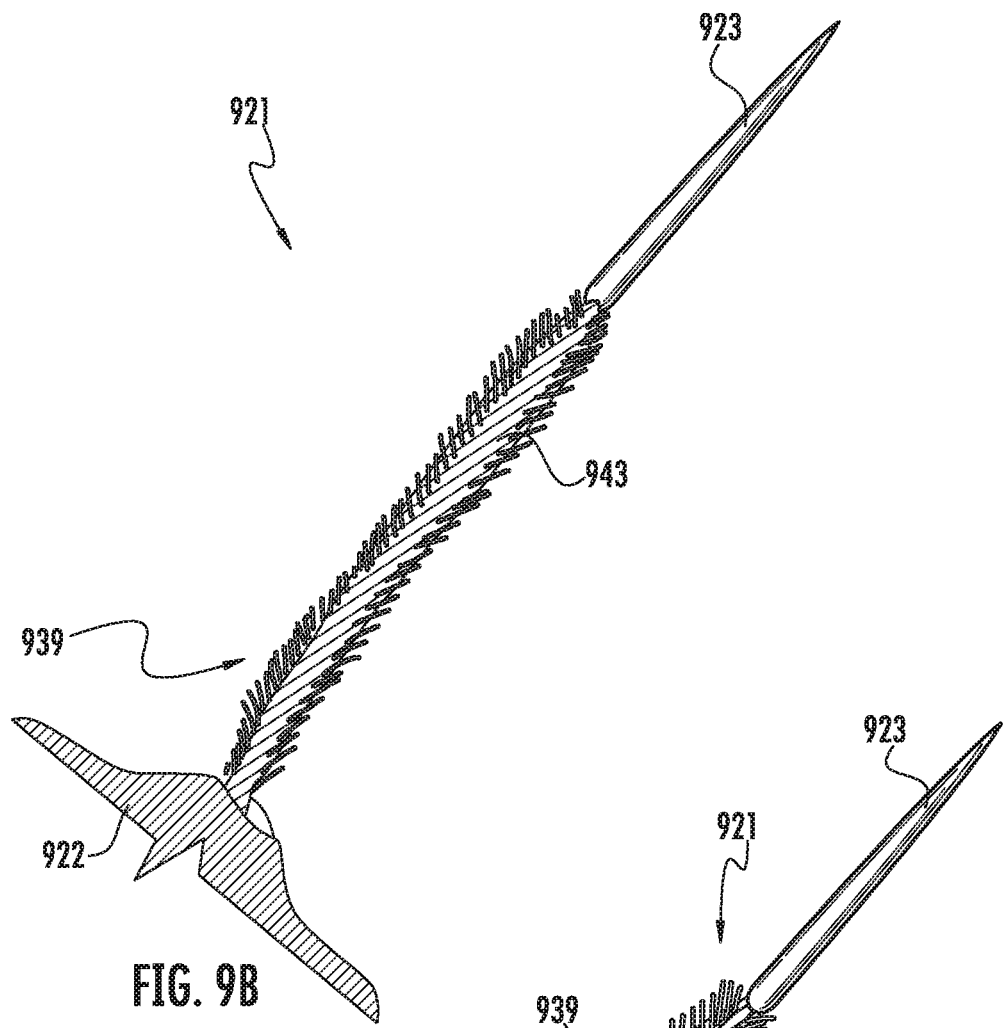

Turning now to FIGS. 9A-9D, a suture 921 according to embodiments of the present disclosure will be described. The suture 921 may include a rigid tip 923 connected to a polymer body 939, wherein the polymer body 939 may be rigid or flexible. As shown in FIG. 9A, the suture 921 may initially pass through at an interface 933 of the target tissue 922 in a direction shown by arrow 927. In this configuration, the polymer body 939 is generally straight and elongated. However, as demonstrated in FIG. 9B, an outer material 943 of the polymer body 939 may expand or grow radially when it comes into contact with a fluid (not shown), such as water, saline, blood, etc.

In some embodiments the outer material 943 of the polymer body 939 may be a hydrogel. The term "hydrogel" may indicate a crosslinked, water insoluble, water containing material. Suitable cross-linkable polymers include but are not limited to one or a mixture of polymers selected from the group consisting of polyhydroxy ethyl methacrylate, polyvinyl alcohol, polyacrylamide, poly (N-vinyl pyrrolidone), polyethylene oxide, hydrolysed polyacrylonitrile, polyacrylic acid, polymethacrylic acid, polyethylene amine, alginic acid, pectinic acid, carboxy methyl cellulose, hyaluronic acid, heparin, heparin sulfate, chitosan, carboxymethyl chitosan, chitin, pullulan, gellan, xanthan, carboxymethyl starch, carboxymethyl dextran, chondroitin sulfate, cationic guar, cationic starch as well as salts and esters thereof. The hydrogel produces may have having improved mechanical properties, such as improved stiffness, modulus, yield stress, strength, etc., at the interface 933.

Figure 9C:
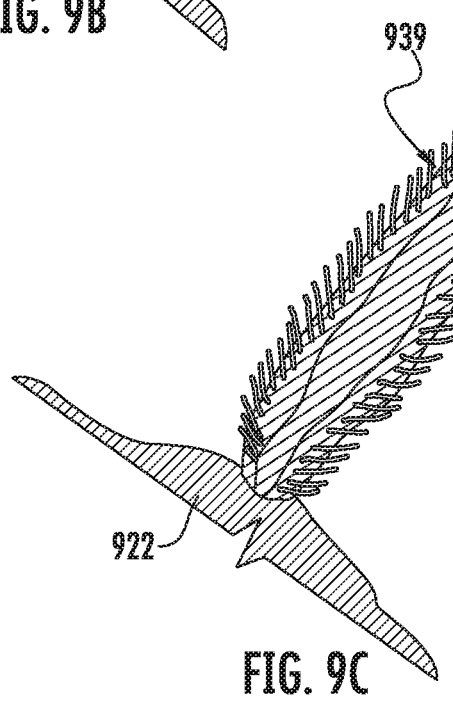
Figure 9D:
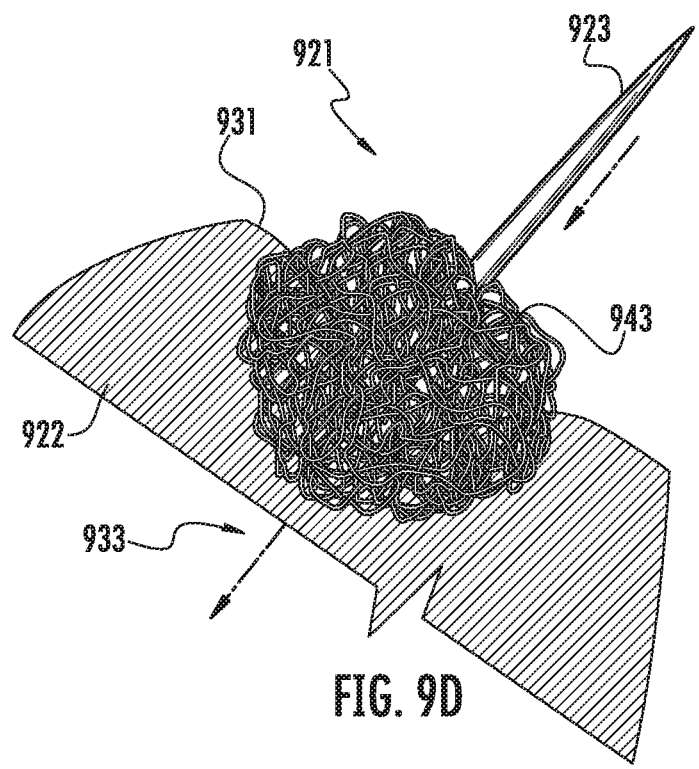

As shown in FIG. 9C, as the suture 921 is retracted, the outer material 943 of the polymer body 939 begins to bunch. Further retraction of the suture 921 towards the target tissue 922, as demonstrated in FIG. 9D, causes the outer material 943 to gather as a bundle along a surface 931 of the target tissue 922. The interface 933 between the outer material 943 and the target tissue 922 generally has a larger area due to the expansion of the outer material 943. Force is therefore better distributed at the interface 933, making it less likely that the target tissue 922 will rupture.

Figure 10A:
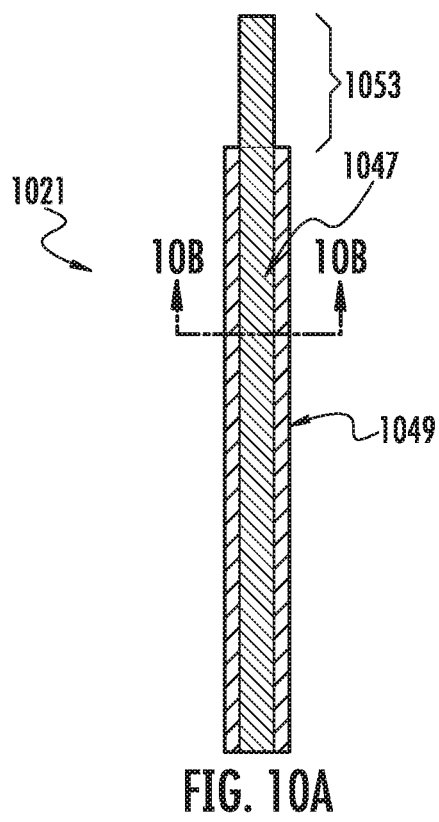
FIG. 10A is a side view of an example suture according to embodiments of the present disclosure.
Figure 10B:
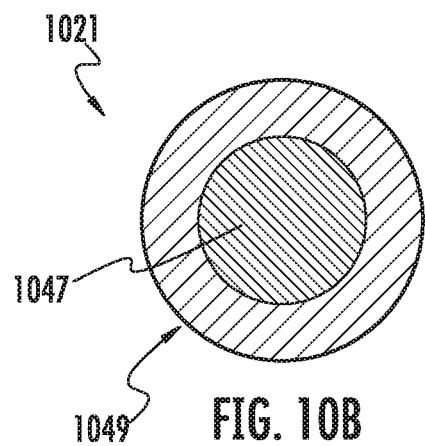
FIG. 10B is a top cross-sectional view of the suture of FIG. 10A, according to embodiments of the present disclosure.
Figure 10C:
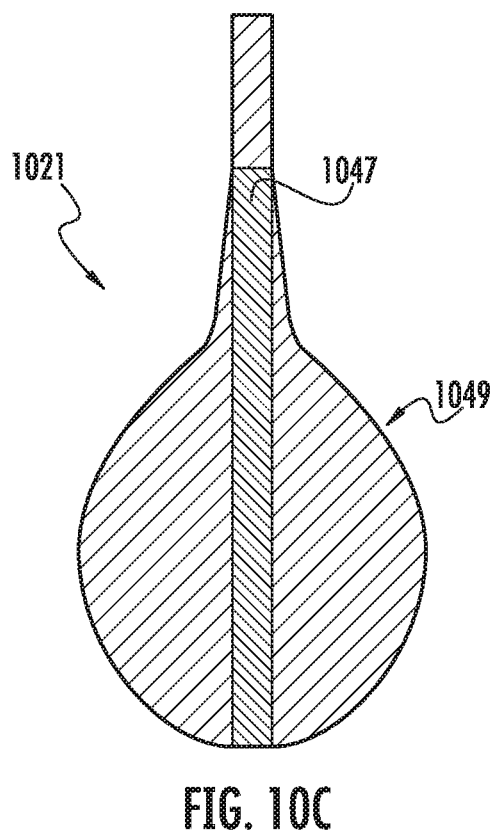
FIG. 10C is a side view of the suture of FIG. 10A following retraction of the suture, according to embodiments of the present disclosure.

Turning now to FIGS. 10A-10C, a suture 1021 according to embodiments of the present disclosure will be described. As shown, the suture 1021 may include a core 1047 surrounded by a sheath 1049. A portion of the core 1047 extending outside of the sheath 1049 may correspond to a tip 1053 of the suture 1021. In some embodiments, the sheath 1049 is capable of expanding radially from the core 1047. Furthermore, the sheath 1049 may move independent of the core 1047 to allow for bunching of the sheath, as demonstrated in FIG. 10C. In this embodiment, the sheath 1049 may be a continuous or sheet-like covering that bulbs and buckles upon expansion and retraction of the core 1047, creating a solid plug-like interface where the suture 1021 meets a target tissue (not shown). In some embodiments, the sheath 1049 is disposed concentrically around the core 1047.

Figure 11A:
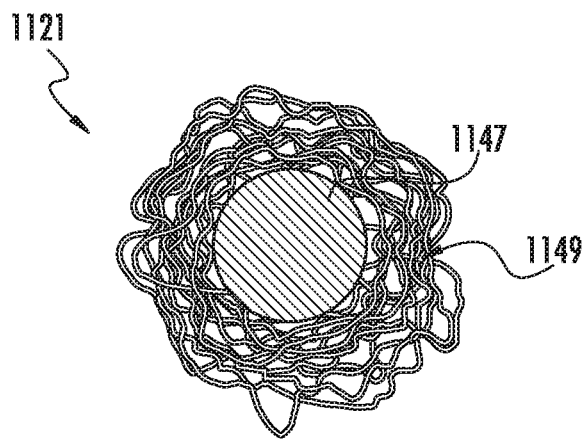
FIG. 11A is a top cross-sectional view of an example suture according to embodiments of the present disclosure.
Figure 11B:
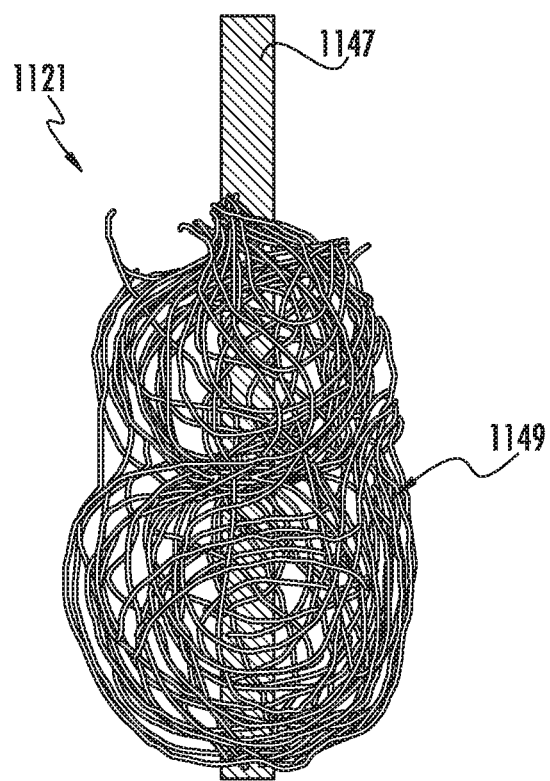
FIG. 11B is a side view of the suture of FIG. 11A following retraction of the suture, according to embodiments of the present disclosure.

In the embodiment of FIGS. 11A-11B, a sheath 1149 of a suture 1121 may include a plurality of flexible strands. As shown, as a core 1147 of the suture 1121 is retracted, the flexible strands bunch-up, expanding to create a mesh-like network with increased surface area. In some embodiments, the sheath 1149 is disposed concentrically around the core 1147.

Figure 12A:
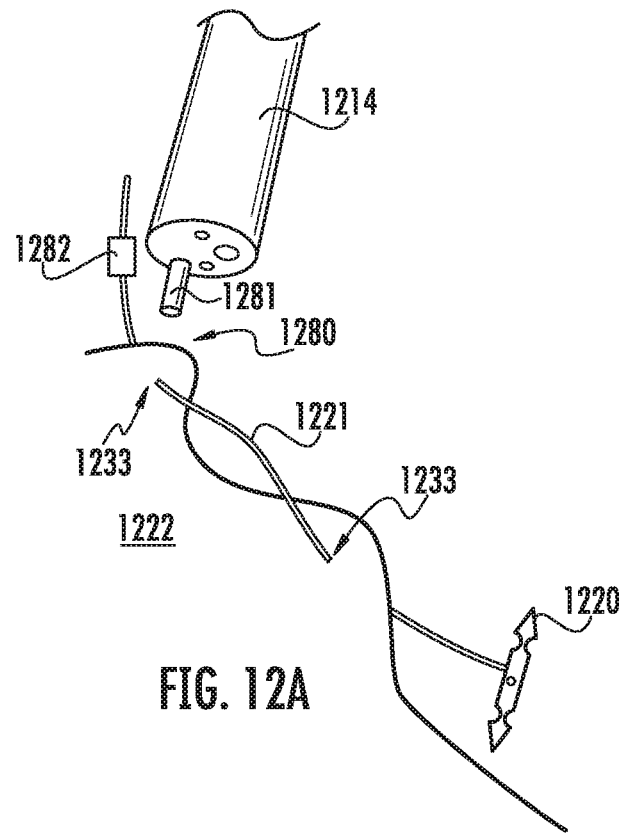
FIGS. 12A-12B are perspective views demonstrating use of a sprayable adhesive applied to an area of tissue according to embodiments of the present disclosure.
Figure 12B:
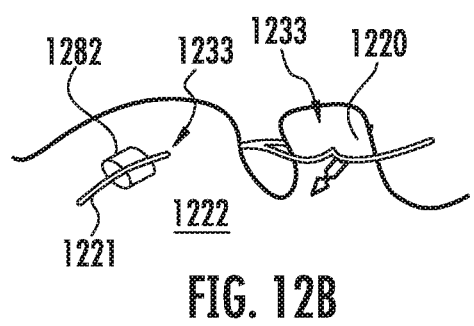

Turning now to FIGS. 12A-12B, the use of a sprayable adhesive 1280 applied to an area of target tissue 1222 according to embodiments of the present disclosure will be described in greater detail. As shown, a sprayable adhesive 1280 may be delivered through an endoscope 1214. The sprayable adhesive 1280 may be applied to the target tissue 1222 at each interface 1233 where the suture 1221 and the needle 1220 penetrate the target tissue 1222. As a result, the interface 1233 may be less susceptible to tearing under the pull of the suture 1221.

During use, a physician may conduct an endoscopic procedure. The physician may retract a device occupying the working channel (e.g., visualization device) and advance a needle or catheter 1281. Once this feature reaches the working channel, a syringe (not shown) with a medical grade, silicone-based spray adhesive, for example, would be coupled to the proximal end of the catheter 1281 (e.g., via a Luer connector). The syringe may be actuated, forcing the sprayable adhesive 1280 to eject from the distal end of the endoscope 1214. As shown in FIG. 12B, as the sprayable adhesive sets, the surface of the target tissue 1222 that a cinch 1282 and needle 1220 are in contact with will harden and prevent expansion, thus preventing the cinch 1282 and/or needle 1220 from passing through the hole in the target tissue 1222 at each interface 1233.

Figure 13A:
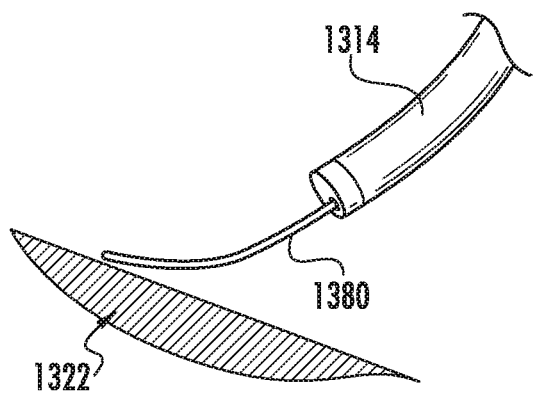
FIGS. 13A-13C are perspective views demonstrating use of a glue applied to an area of tissue according to embodiments of the present disclosure.
Figure 13B:
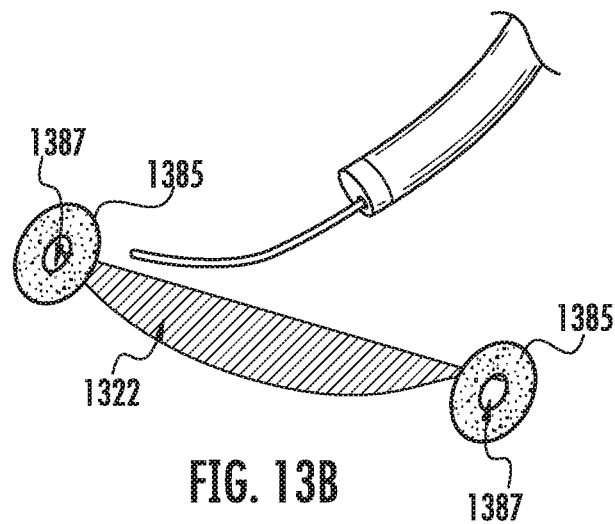
Figure 13C:
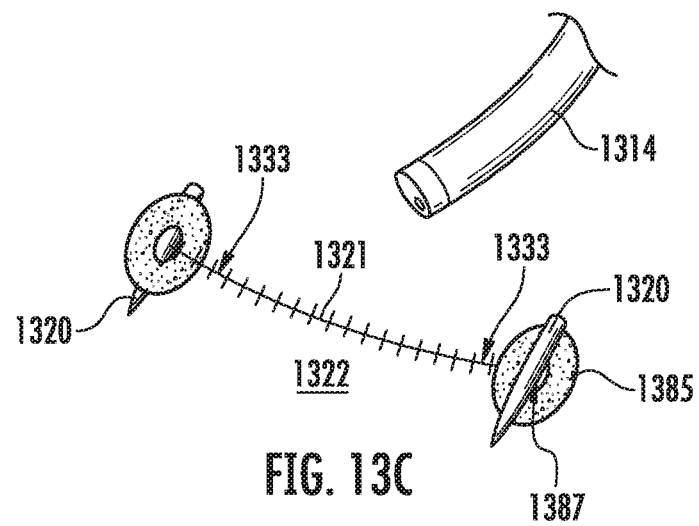

In the non-limiting embodiment of FIGS. 13A-13C, a curable glue 1380 (e.g., moisture or UV curable) may be added to a target tissue 1322 at each end of a suture 1321 to distribute force applied on an interface 1333 between the target tissue 1322 and the suture 1321. Due to the flexible nature of the curable glue 1380 prior to curing, the curable glue 1380 can more easily pass through the working channel of the endoscope 1314 and be applied at the target tissue 1322. In addition, the curable glue 1380 may allow the physician to better customize a final shape for the curable glue 1380 based on the demands of the procedure, location of the wound, his/her preference, etc. For example, as shown in FIGS. 13B-13C, the curable glue 1380 may be fashioned into one or more cylindrical washers 1385 each having a central opening 1387. As a result, the suture 1321 (FIG. 13C) may pass through the central openings 1387. Furthermore, use of the curable glue 1380 also gives the physician the freedom to add additional glue at various points in the procedure, for example, to improve the force distribution as needed pre- or post-suturing. In some embodiments, as shown in FIG. 13C, the needle 1320 may remain on top of the curable glue 1380 following suturing. To improve visibility, the curable glue 1380 can also be dyed in alternative embodiments.

Figure 14A:
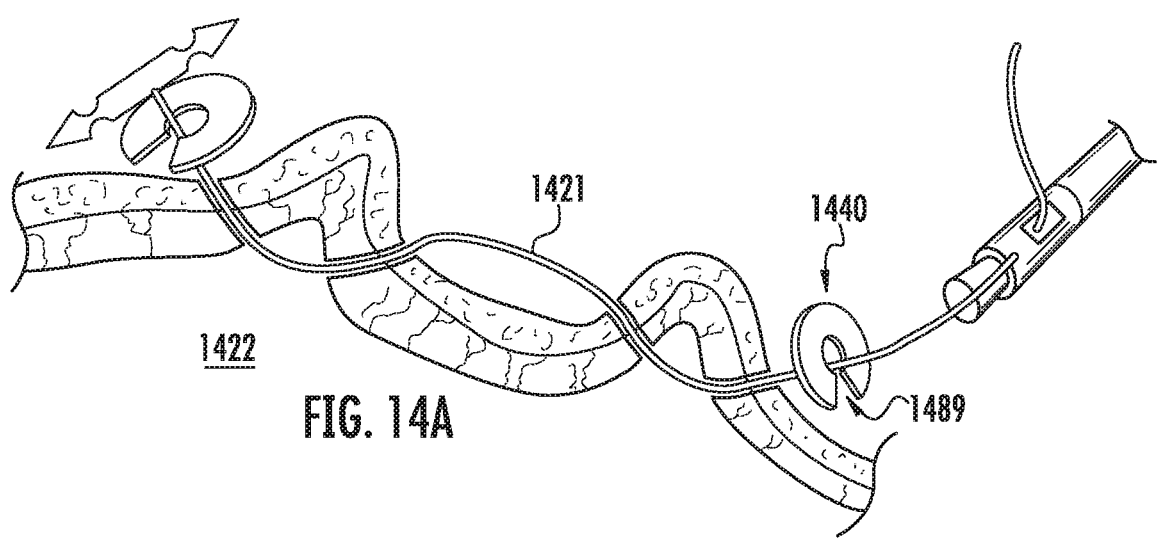
FIG. 14A is a perspective view demonstrating use of tubular tissue supports according to embodiments of the present disclosure.
Figures 14B, 14C:
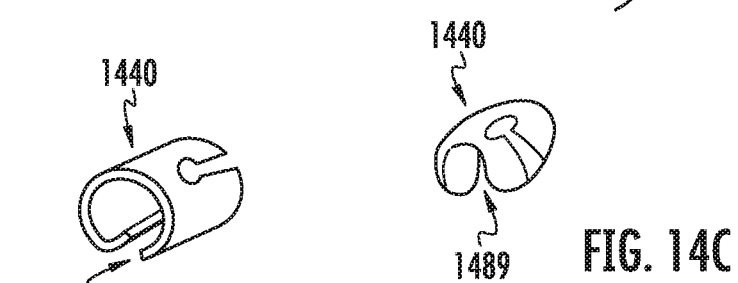
FIG. 14B is a perspective view an example tubular tissue support according to embodiments of the present disclosure.
FIG. 14C is a perspective view another example tubular tissue support according to embodiments of the present disclosure.

In the non-limiting embodiment of FIGS. 14A-14C, one or more tubular tissue supports (e.g., washers) 1440 may be used on opposite sides of a target tissue 1422. As shown, the tubular tissue supports 1440 may include a slot 1489 through which a suture 1421 can run, allowing the tubular tissue supports 1440 to be placed anywhere along the suture 1421 after the suture 421 is threaded through the target tissue 1422. In some embodiments, the tubular tissue supports 1440 may be delivered endoscopically and maneuvered into place using a grasper or similar tool to protect the target tissue 1422 after the suture 1421 is placed, but before the suture 1421 is cinched.

Figure 15:
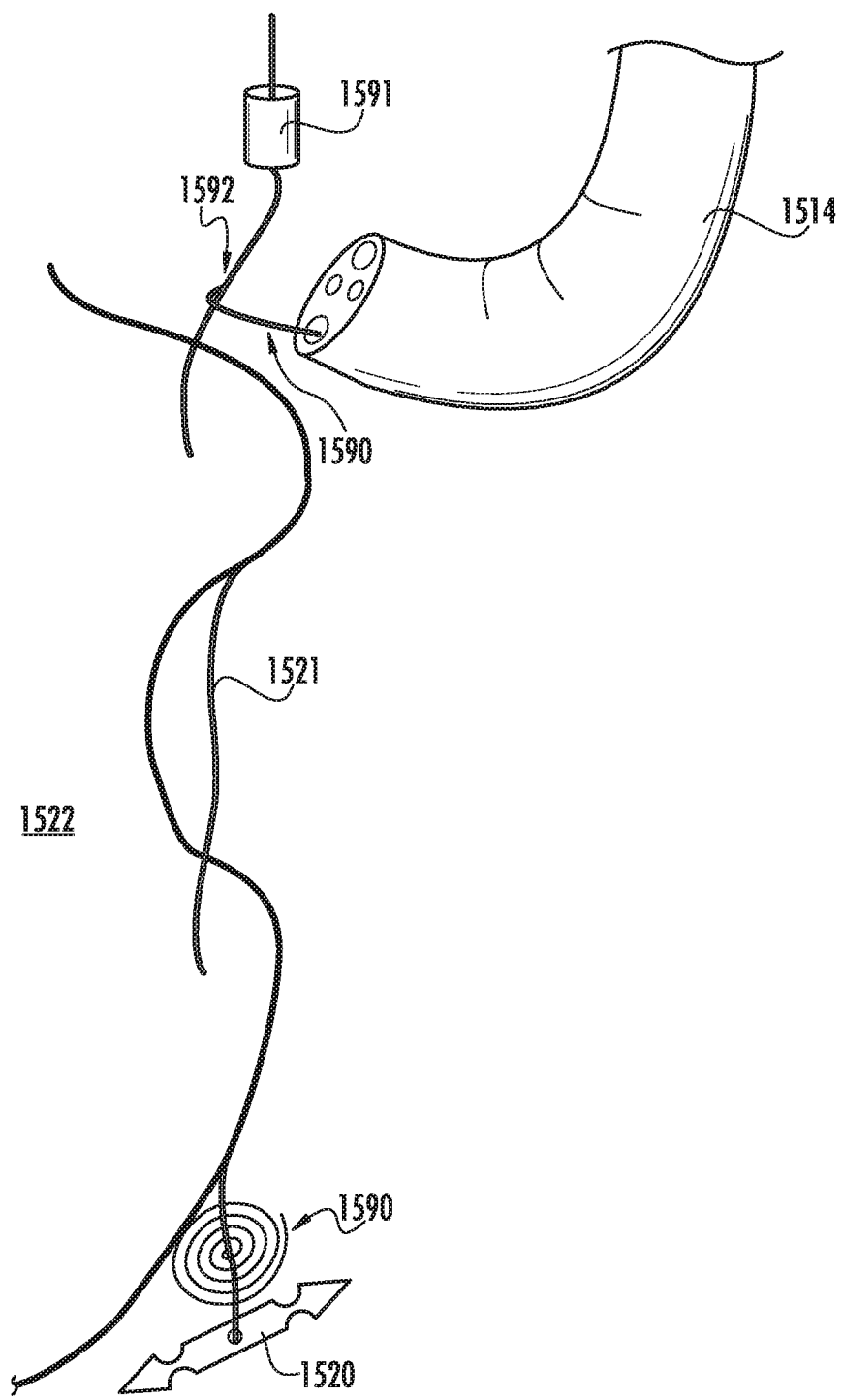
FIG. 15 is a perspective view illustrating the use of spring-loaded wires according to embodiments of the present disclosure.

Turning now to FIG. 15, tissue supports in the form of one or more elastic elements or spring-loaded wires will be described. As shown, a wire 1590 may be deployed from an endoscope 1514 and onto a suture 1521 as a needle 1520 and the suture 1521 traverse through a target tissue 1522. In the non-limiting embodiment shown, the wire 1590 may be a metallic, spring-loaded wire with shape memory, which is preloaded into a delivery catheter of the endoscope 1514. As the wire 1590 is advanced beyond a distal tip of the endoscope 1514, it begins to curl. The wire 1590 may create a hook 1592 as it begins to curl, the hook being engageable with the suture 1521 between the cinch 1591 and the target tissue 1522, and/or between the needle 1520 and the target tissue 1522.

Once the suture 1521 is acquired by the hook 1592, the rest of the wire 1590 may be fed out of the endoscope 1514. The wire 1590 continues to curl until a proximal end is expelled. Use of the wire 1590 allows for a low-profile during delivery and, once deployed, a large solid surface area for the cinch 1591 and the needle 1520 to interface with, thus preventing pull through. In non-limiting embodiments, the wire 1590 may be made of steel, Nitinol or any other material with a high spring constant. In other embodiments, the wire 1590 may also take on the profile of a ribbon, which may also increase a contact surface area between the wire 1590 and the cinch 1591 and the needle 1520.

Alternatively, the wire 1590 could be a bi-stable spring that is straight in one orientation and curved in another. The wire 1590 may be advanced until it is positioned between the cinch 1591 and the needle 1520. Once positioned appropriately, the spring may be shifted to a second orientation, causing it to curve into a coil or spiral-like orientation.

Turning now to FIG. 16, a method 1600 according to embodiments of the present disclosure will be described in greater detail. At block 1601, the method may include passing a needle and a suture of a tissue suturing device through a target tissue, the tissue suturing device extending from a distal end of an endoscope. In some embodiments, the plurality of tissue supports are housed within a deployment device, wherein a first tissue support is exposed within a suture cavity. In some embodiments, the deployment device may be a cartridge or collar. In some embodiments, a cover may extend across the deployment device, the cover including an opening to permit access to the plurality of tissue supports by a needle. In some embodiments, the tissue supports may include one or more of the following: a flexible washer, an adhesive, a pledget, and an elastic or spring-loaded wire.

At block 1603, the method 1600 may include deploying a first tissue support from the tissue suturing device to a position along a first portion of the target tissue. In some embodiments, the first tissue support may be engaged within the suture cavity by the needle to remove the first tissue support from the deployment device. At block 1605, the method 1600 may include deploying a second tissue support from the tissue suturing device to a position along a second portion of the target tissue, wherein tightening the suture brings the first tissue support and the second tissue support closer together.

Although the illustrative method 1600 is described above as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure. Furthermore, the method 1600 may be implemented in association with the formation and/or processing of structures illustrated and described herein as well as in association with other structures not illustrated.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

As used herein, the singular forms "a," "an," and "the" are intended to include the plural forms as well, unless the context clearly indicates otherwise. It will be further understood that the terms, "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Furthermore, the terms "substantial" or "substantially," as well as the terms "approximate" or "approximately," can be used interchangeably in some embodiments, and can be described using any relative measures acceptable by one of skill. For example, these terms can serve as a comparison to a reference parameter, to indicate a deviation that will still provide the intended function. Although non-limiting, the deviation from the reference parameter can be, for example, in an amount of less than 1%, less than 3%, less than 5%, less than 10%, less than 15%, less than 20%, and so on.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A tissue suturing apparatus for an endoscope, comprising:
   a tissue suturing device extending from a distal end of the endoscope, the tissue suturing device comprising a plurality of tissue supports, wherein each of the plurality of tissue supports is deployable towards a target tissue, and wherein one or more tissue supports of the plurality of tissue supports is configured to receive a suture during deployment;
   a deployment device comprising: a housing containing the plurality of tissue supports; and a cover extending across the housing, the cover including an opening to permit access to the plurality of tissue supports by a needle attached to the suture, wherein the plurality of tissue supports is contained within the deployment device prior to deployment; and
   the needle, wherein the needle engages a tissue support of the plurality of tissue supports to deploy the tissue support,
   the deployment device comprising an interior channel and a biasing device for biasing the plurality of tissue supports within the interior channel, wherein the plurality of tissue supports are arranged end-to-end within the interior channel.

2. The tissue suturing apparatus of claim 1, the suture comprising:
   a core; and
   a sheath, wherein the sheath is operable to expand radially from the core in an area adjacent the target tissue.

3. The tissue suturing apparatus of claim 2, wherein the sheath comprises a plurality of flexible strands.

4. The tissue suturing apparatus of claim 1, wherein the plurality of tissue supports comprises one or more of a flexible washer, a sprayable adhesive, a pledget, or a spring-loaded wire.

5. A tissue suturing device, comprising:
   a deployment device;
   a plurality of tissue supports deployable from the deployment device towards a target tissue, wherein the plurality of tissue supports includes a central opening for receiving a suture during deployment;
   a fixed end secured to a distal end of an endoscope;
   a free end opposite the fixed end, wherein the deployment device is coupled to one of the fixed end or the free end;
   a housing surrounding the plurality of tissue supports, the housing comprising an interior channel and a biasing device for biasing the plurality of tissue supports within the interior channel, wherein the plurality of tissue supports are arranged end-to-end within the interior channel; and a cover extending across the housing, the cover including an opening for access to the plurality of tissue supports by a needle attached to the suture.

6. The tissue suturing device of claim 5, the suture comprising:
   a core; and
   a sheath, wherein the sheath is operable to expand radially from the core in an area adjacent the target tissue.

7. The tissue suturing device of claim 6, wherein the sheath comprises a plurality of flexible strands.

8. The tissue suturing device of claim 5, wherein the plurality of tissue supports comprises one or more of a flexible washer, a sprayable adhesive, a pledget, or a spring-loaded wire.

\* \* \* \* \*